US00PP35372P2

(12) United States Plant Patent
Van Dijk

(10) Patent No.: US PP35,372 P2
(45) Date of Patent: Sep. 5, 2023

(54) ***ANTHURIUM* PLANT NAMED 'AN2887337'**

(50) Latin Name: ***Anthurium andraeanum* L.**
Varietal Denomination: AN2887337

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,967

(22) Filed: Feb. 10, 2023

(51) Int. Cl.
*A01H 5/02* (2018.01)
*A01H 6/10* (2018.01)

(52) U.S. Cl.
USPC ..... Plt./366

(58) Field of Classification Search
USPC ..... Plt./366, 365
See application file for complete search history.

*Primary Examiner* — Karen M Redden
(74) *Attorney, Agent, or Firm* — Jondle & Associates, P.C.

(57) ABSTRACT

A new *Anthurium* plant named 'AN2887337' particularly distinguished by having medium shiny and medium blistered, white, oblong-cordate, and durable spathes that retain the original color for a very long period of time, medium shiny, dark green and narrowly-long cordate, durable leaves, white spadix with yellow-green tips, early and rich flowering continuously throughout the year, and a plant height of 70.0 cm to 80.0 cm is disclosed.

3 Drawing Sheets

Genus and species: *Anthurium andraeanum* L.
Variety denomination: 'AN2887337'.

BACKGROUND OF THE NEW PLANT

The present invention comprises a new and distinct variety of *Anthurium*, botanically known as *Anthurium andraeanum* L., and hereinafter referred to by the variety name 'AN2887337'. The new *Anthurium* plant is a product of a planned breeding program conducted by the inventor in Bleiswijk, the Netherlands. The objective of this breeding program was to create a new plant with a height of 70.0 cm to 80.0 cm having medium blistered, medium shiny, white, oblong-cordate, and durable spathes.

The new variety originated from a cross-pollination made in February 2007 in Bleiswijk, the Netherlands. The female parent was a pink *Anthurium* pot plant designated '05-007714-0001' (unpatented), and the male parent was a white *Anthurium* pot plant '04-006693-0003' (unpatented).

A single plant was selected from the progeny of the stated cross in October 2010. Asexual reproduction of the new variety by tissue culture in 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 19, 2021 (Application no. 2021/2974), by Applicant who obtained the subject matter disclosed directly from the inventor. 'AN2887337' has not been made publicly available or sold anywhere in the world prior to the effective filing date of this application with the exception of sales or disclosures made one year or less before the effective filing date of this claimed invention by Applicant who obtained 'AN2887337' directly from the inventor.

SUMMARY OF THE INVENTION

The following are the most outstanding and distinguishing characteristics of this new variety when grown under normal horticultural practices in Bleiswijk, the Netherlands:

1) Medium blistered, medium shiny, white, oblong-cordate spathes;
2) White spadices with yellow and green tips;
3) Medium shiny, dark green, narrowly-long cordate leaves;
4) Spathes: relative position of lobes is incurved, but not touching; and
5) Spathes: angle of distal part to the peduncle is obtuse.

DESCRIPTION OF THE PHOTOGRAPHS

This new *Anthurium* plant is illustrated by the accompanying photographs which show the overall plant habit including blooms, buds, and foliage of the plant; the colors shown are as true as can be reasonably obtained by conventional photographic procedures. The photographs are of a 60-week-old plant grown in a greenhouse in Bleiswijk, the Netherlands, in November 2022. Colors in the photographs may differ from the color values cited in the detailed botanical description, which accurately describe the actual colors of the new variety.

DESCRIPTION OF THE NEW VARIETY

Figure 1:
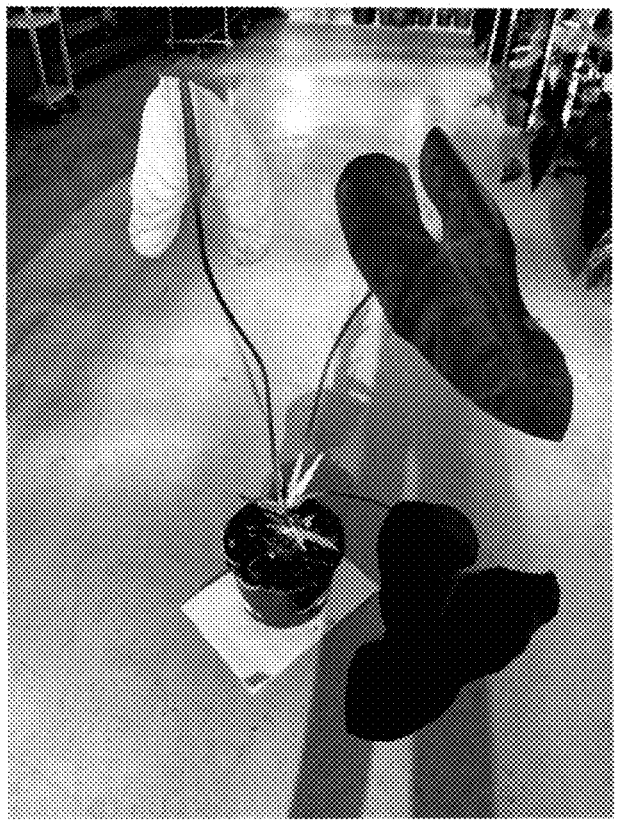
FIG. 1 shows the overall plant habit, including blooms, buds, and foliage.
Figure 2:
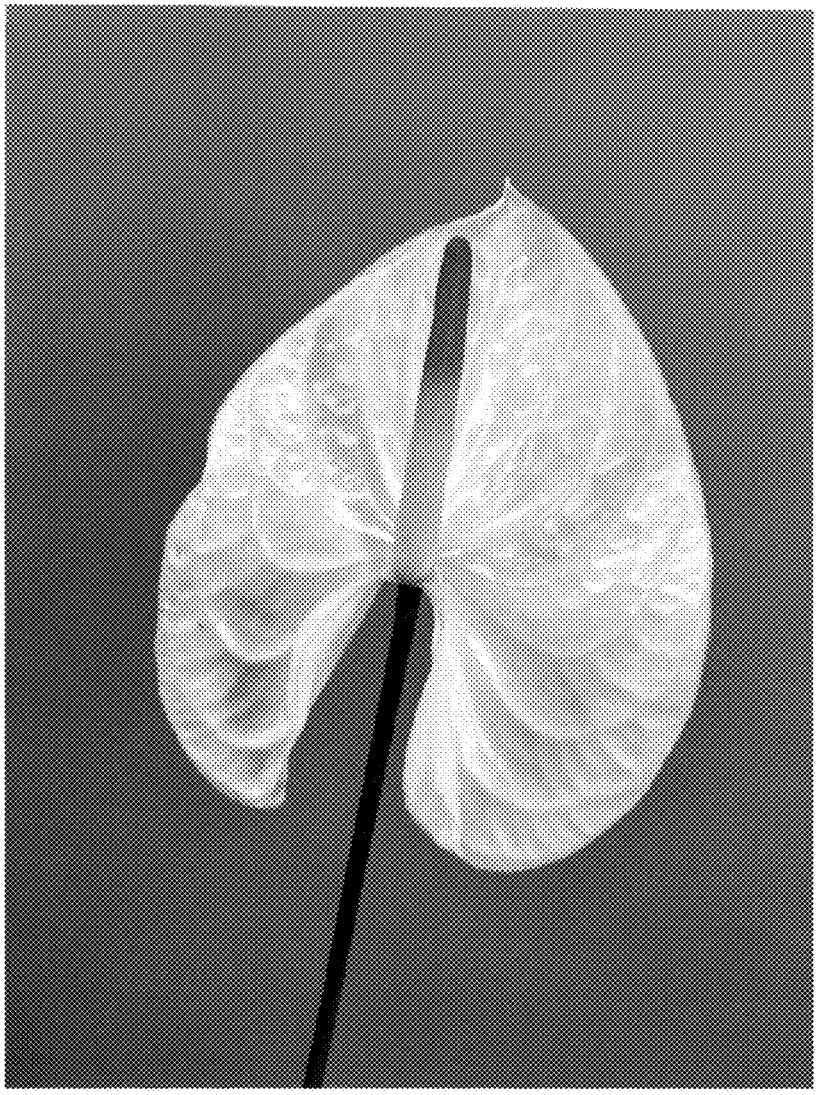
FIG. 2 shows a close-up of the mature spathe.
Figure 3:
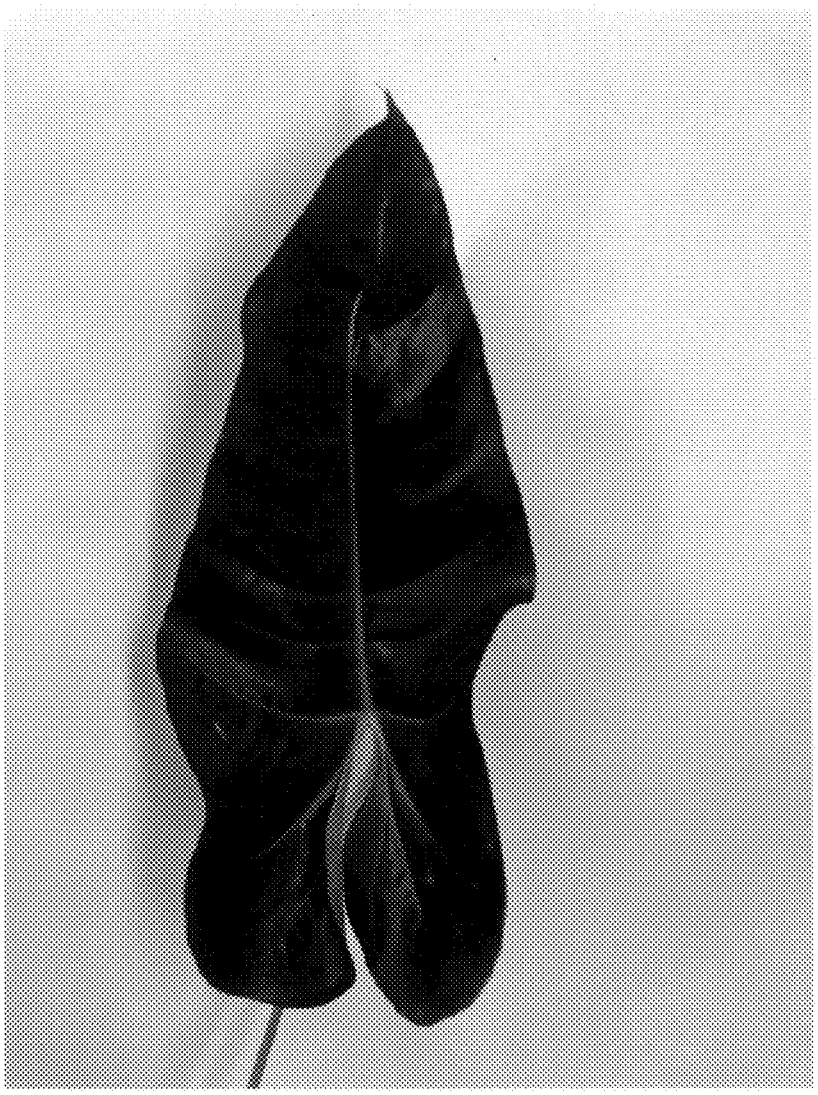
FIG. 3 shows a close-up of the upper leaf blade surface.

The following detailed description sets forth the distinctive characteristics of 'AN2887337'. The data which define these characteristics were collected from asexual reproductions carried out in Bleiswijk, the Netherlands. The plant history was taken on 60-week-old plants which were planted from tissue culture in 17-centimeter (diameter) pots and grown in a glass greenhouse between 19° C. and 24° C. Observations were made in November 2022. Color readings were taken under 5000 lux natural light in the greenhouse.

Color references are primarily to The R.H.S. Colour Chart of The Royal Horticultural Society of London (RHS) (2015).

DETAILED BOTANICAL DESCRIPTION

Classification:

*Family.*—Araceae.

*Botanical.*—*Anthurium andraeanum* L.

*Common name.*—*Anthurium.*

*Denomination.*—'AN2887337'.

Parentage:

*Female parent.*—*Anthurium* plant '05-007714-0001' (unpatented).

*Male parent.*—*Anthurium* plant '04-006693-0003' (unpatented).

Plant:

*Propagation.*—Tissue culture.

*Root description.*—Fleshy-creamy (RHS 161B) colored roots with small hairy lateral roots having light creamy (RHS 161D) colored root tips.

*Time to produce a finished flowering plant.*—55 to 66 weeks after planting in a 17-cm (diameter) pot.

*Growth habit.*—Upright.

*Height (measured from soil, including inflorescence).*—70.0 cm to 80.0 cm.

*Width (measured from leaf tips).*—55.0 cm to 65.0 cm.

Leaves:

*Immature leaves.*—Length: 27.0 cm to 30.0 cm. Width: 12.0 cm to 14.0 cm. Color: Upper surface: RHS 146B. Lower surface: RHS 146C. Texture (both upper and lower surfaces): Leathery, soft, thin, and strongly glossy.

*Mature leaves.*—Length (fully expanded): 30.0 cm to 33.0 cm. Width: 14.0 cm to 16.0 cm. Shape: Narrowly long cordate. Apex: Abruptly acuminate. Base: Cordate. Leaf blade angle with the petiole: Between 100 degrees and 120 degrees. Leaf margin: Entire. Color: Upper surface: RHS 147A. Lower surface: RHS 146B. Texture (both upper and lower surfaces): Leathery, thick, smooth, and weakly glossy. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes.*—Present. Arrangement: Leaf blade has two lobes extending past the petiole. The lobes are overlapping. Length of lobes of mature leaf blades: 8.5 cm to 9.5 cm. Width of lobes of mature leaf blades: 8.0 cm to 8.5 cm. Distance from petiole/leaf junction to highest point on lobes of mature leaf blades: 7.0 cm to 8.0 cm.

*Petiole.*—Cross-section: Round. Diameter: 0.2 cm to 0.3 cm. Length: 53.0 cm to 58.0 cm for a mature leaf size. Color: Mature leaf: RHS 144A. Immature leaf: RHS 144B. Cataphyll color surrounding the petiole: Outside: RHS 144B. Inside: RHS 145C.

*Geniculum.*—Length: 2.5 cm to 3.0 cm. Width: 0.3 cm to 0.4 cm. Color: RHS 144B.

Inflorescence:

*Arrangement.*—Single.

*Flowering habit (length of flowering season).*—Continuous.

*Number of inflorescences per plant.*—4 to 6 flowers in a period of one year.

*Fragrance.*—Absent.

*Longevity of inflorescence as a cut flower.*—26 to 31 days.

Spathe:

*Buds.*—The spathe is tightly rolled around the spadix and extrudes from the peduncle sheath.

*Arrangement.*—Spathe angle with the peduncle is between 150 degrees and 160 degrees; the spathe stands on a wiry peduncle about 15.0 cm to 25.0 cm above the foliage.

*Shape.*—Oblong cordate.

*Apex.*—Acuminate.

*Base.*—Cordate.

*Texture.*—Medium blistered and medium shiny.

*Margin.*—Undulated.

*Size.*—Length: 13.0 cm to 14.0 cm. Width: 16.0 cm to 17.0 cm.

*Lobes.*—Present. Arrangement: The spathe has two lobes extending past the peduncle. The lobes are incurved, but non-touching. Length: 5.5 cm to 6.5 cm. Width: 6.5 cm to 7.5 cm.

*Color.*—Just fully open: Upper surface: RHS NN155A. Lower surface: RHS NN155B. This white color remains for a very long period, at least more than 30 weeks after opening.

Peduncle:

*Shape.*—Erect.

*Cross-section.*—Round.

*Length.*—65.0 cm to 70.0 cm.

*Diameter.*—0.3 cm to 0.4 cm.

*Color.*—RHS 144B.

Flowering time:

*General.*—One small, rooted, untreated tissue culture plant of 4.0 cm tall will flower for the first time, depending on the season, after 30 to 35 weeks.

Spadix:

*Size.*—Length: 7.5 cm to 8.5 cm (depending on flower size). Width (at apex): 0.3 cm to 0.4 cm. Width (at base): 0.4 cm to 0.6 cm.

*Shape.*—Columnar.

*Angle of spadix tip with peduncle.*—160 degrees to 180 degrees.

*Texture.*—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color.*—Immature: Yellow toward the tip (RHS 13A) and yellowish-green tip (RHS N144A). Mature: RHS NN155A. Ages to: RHS 144A.

Flowers:

*Quantity per spadix.*—450 to 500.

*Spadix flower arrangement.*—Bisexual, rounded in cross-section.

*Shape.*—Rounded.

*Size.*—Length: 0.05 cm to 0.1 cm. Diameter (maximum): 0.10 cm.

*Color.*—RHS 158D.

Reproductive organs:

*Stamens.*—Not visible.

*Pollen amount.*—Absent.

*Pistil.*—Quantity: 450 to 500. Length: Less than 0.01 cm. Color: RHS 158D.

*Style.*—Not observed to date.

*Stigma.*—Shape: Ovoid. Diameter: Less than 0.01 cm. Color: RHS 158D.

*Ovary.*—Rarely visible.

*Ovary color.*—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2887337'differs from the female parent plant '05-007714-0001' (unpatented) in that "AN2887337' has white spathes that are incurved, but not touching, whereas '05-007714-0001' has pink spathes that are adpressed.

'AN2887337' differs from the male parent plant '04-006693-0003' (unpatented) in that 'AN2887337' has medium to long spadices with medium tapering toward the top, whereas '04-006693-0003' has short to medium spadices with very weak tapering toward the top.

'AN2887337' differs from similar commercial variety 'ANTHAQXM' (unpatented) in that 'AN2887337' has green cataphyll, medium to long spadices, and narrowly-long cordate leaves, whereas 'ANTHAQXM' has red cataphyll, very long spadices, and elliptical-cordate leaves.

'AN2887337' differs from similar variety 'ANTHAQUIRE' (unpatented) in that the angle of spadix tip with peduncle for AN2887337' is 160 degrees to 180 degrees and narrowly-long cordate leaves that are overlapping, whereas the angle of spadix tip with peduncle for 'ANTHAQUIRE' is 120 degrees to 130 degrees and elliptical-cordate to narrowly-long cordate leaves that are incurved, but not touching.

I claim:

1. A new and distinct variety of *Anthurium* plant named 'AN2887337', substantially as illustrated and described herein.

* * * * *